United States Patent [19]
Tweden et al.

[11] Patent Number: 5,895,419
[45] Date of Patent: Apr. 20, 1999

[54] COATED PROSTHETIC CARDIAC DEVICE

[75] Inventors: Katherine S. Tweden, Mahtomedi, Minn.; William R. Holmberg, New Richmond, Wis.; Darrin J. Bergman; Terry L. Shepherd, both of Shoreview, Minn.

[73] Assignee: St. Jude Medical, Inc., St. Paul, Minn.

[21] Appl. No.: 08/791,890

[22] Filed: Jan. 31, 1997

Related U.S. Application Data

[63] Continuation-in-part of application No. 08/722,661, Sep. 30, 1996, abandoned.
[51] Int. Cl.$^6$ ............................................. A61F 2/24
[52] U.S. Cl. ....................................... 623/2; 623/900
[58] Field of Search .............................. 623/1, 2, 3, 900, 623/11, 12

[56] References Cited

U.S. PATENT DOCUMENTS

| | | | |
|---|---|---|---|
| 4,054,139 | 10/1977 | Crossley | 128/260 |
| 4,403,604 | 9/1983 | Wilkinson et al. | 128/1 |
| 4,428,375 | 1/1984 | Ellman | 128/334 |
| 4,483,688 | 11/1984 | Akiyama | 604/265 |
| 4,581,028 | 4/1986 | Fox, Jr. et al. | 623/2 |
| 5,207,706 | 5/1993 | Menaker | 623/1 |
| 5,468,562 | 11/1995 | Farivar et al. | 428/457 |
| 5,474,797 | 12/1995 | Sioshansi | 427/2.24 |
| 5,520,664 | 5/1996 | Bricault, Jr. et al. | 604/265 |
| 5,603,337 | 2/1997 | Jarvik | 128/898 |

FOREIGN PATENT DOCUMENTS

| | | |
|---|---|---|
| 2 226 762 | 3/1988 | United Kingdom . |
| WO 93/23092 | 11/1993 | WIPO . |

OTHER PUBLICATIONS

"New Processes for Surface Treatment of Catheters", by P. Sioshansi, *Artificial Organs*, vol. 18, No. 4, 1994, pp. 266–271.

"Biocompatibility of Silver-Coated Polyurethane Catheters and Silver-Coated Dacron® Material", by A. Olofs, C. Grosse-Siestrup, S. Bisson, M. Rinck, R. Rudolph and U. Gross, *Biomaterials*, vol. 15, No. 10, 1994, pp. 753–758.

"In Vitro Evaluation of the Antimicrobial Efficacy and Biocompatobility of a Silver-Coated Central Venous Catheter", by B. Jansen, M. Rinck, P. Wolbring, A. Strohmeier and T. Jahns, *Journal of Biomaterials Applications*, vol. 9, Jul. 1994, pp. 55–70.

"Surface Antimicrobial Activity of Heparin-Bonded and Antiseptic-Impregnanted Vascular Catheters", by L. Mermel, S. Stolz and D. Maki, *The Journal of Infectious Diseases*, 1993, pp. 920–924.

"Antibacterial Silver Surfaces–An Assessment of Needs and Opportunities for Clinical Devices", by J. Haynes and T. Schulte, *Proceedings of the First International Conference on Gold and Silver in Medicine*, May 13–14, 1987, p. 331.

"Surgery for Acquired Heart Disease: Surgical Treatment of Prosthetic Valve Endocarditis", by B. Lytle, B. Priest, P. Taylor, F. Loop, S. Sapp, R. Stewart, P. McCarthy, D. Muehreke and D. Cosgrove, *The Journal of Thoracic and Cardiovascular Surgery*, vol. 111, No. 1, Jan. 1996, pp. 198–210.

(List continued on next page.)

*Primary Examiner*—Debra S. Brittingham
*Attorney, Agent, or Firm*—Westman, Champlin & Kelly, P.A.

[57] ABSTRACT

The present invention includes a metallic coating on portions of the prosthesis to enhance the overall acceptability of the implantable device or fabric/sutures used to implant the prosthesis. The preferred metal is silver, which is applied to surfaces which are exposed to the heart tissue. The silver-treated portions of these devices inhibit or greatly reduce colonization of endocarditis-causing bacteria without impacting the overall biocompatibility of the device.

14 Claims, 5 Drawing Sheets

OTHER PUBLICATIONS

"Prevention of Prosthetic Vascular Graft Infection by Rifampicin Impregnation of a Protein–Sealed Dacron Graft in Combination with Parenteral Cephalosporin," by J. Avramovic et al., *J. Cardiovasc Surg.*, 1992, pp. 70–74.

"Prevention of Graft Infection by Use Protheses Bonded with a Rifampin/Collagen Release System," by A. Chervu et al., *Journal of Vascular Surgery*, vol. 14, No. 4, Oct. 1991, pp. 521–525.

"A Passive System Using Rifampin to Create an Infection–Resistant Vascular Prosthesis", by T. Powell, S. Burnham and G. Johnson, Jr., *Surgery*, Nov. 1983, pp. 765–769.

"Treatment of Vascular Graft Infection by In Situ Replacement With a Rifampin–Bonded Gelatin–Sealed Dacron Graft", by O. Goëau–Brissonniére, F. Mercier, M. Nicolas, F. Baccourt, M. Coggia, C. Lebrault and J. Pechére, *Journal of Vascular Surgery*, vol. 19, No. 4, Apr. 1994, pp. 739–744.

"Rifampin Protection Against Experimental Graft Sepsis", by E. McDougal, S. Burnham and G. Johnson, Jr., *Journal of Vascular Surgery*, vol. 4, No. 1, Jul. 1986, pp. 5–7.

"Efficacy and Duration of Antistaphylococcal Activity Comparing Three Antibiotics Bonded to Dacron Vascular Grafts with a Collagen Release System", by A. Chervu, W. Moore, M. Chvapil and T. Henderson, *Journal of Vascular Surgery*, 1991, pp. 897–901.

Catheter Induced Urethal Inflammatory Reaction and Urinary Tract Infection, by H. Liedberg, *Scandinavian Journal of Urology and Nephrology*, 1989, pp. 1–43.

"Antibiotic–Bonded PTFE Vascular Grafts: The Effect of Silver Antibiotic on Bioactivity Following Implantation", by E. Kinney, D. Bandyk, G. Seabrook, H. Kelly and J. Towne, *Journal of Surgical Research*, vol. 50, No. 5, May 1991, pp. 430–435.

"Assessment of Silver–Coated Urinary Catheter Toxicity by Cell Culture", by H. Liedberg and T. Lundeberg, *Urological Research*, 1989, pp. 359–360.

"A Prospective Randomized Trial Comparing the Silver–Impregnanted Collagen Cuff With the Bedside Tunneled Subclavian Catheter", by C. Babycos, A. Barrocas and W. Webb, *Journal of Parenteral and Enteral Nutrition*, vol. 17, No. 1, Feb. 1993, pp. 63–63.

"An Experimental Study on Silver in the Nervous System and on Aspects of its General Cellular Toxicity", by J. Rungby, vol. 37, No. 5, Oct. 1990, pp. 442–449.

"Infections and Thromboembolism with Implantable Cardiovascular Devices", by P. Didisheim, D. Olsen, D. Farrar, P. Portner, B. Griffith, D. Pennington, J. Joist, F. Schoen, A. Gristina and J. Anderson, *Trans. Am. Soc. Artif. Intern. Organs*, 1989, pp. 54–70.

"Sustained Release of Gentamicin From Prosthetic Heart Valves", by L. Olanoff, J. Anderson and R. Jones, *Trans. Am. Soc. Artiff. Intern. Organs*, vol. XXV, 1979, pp. 334–338.

"Cytotoxicity of Amalgams, Alloys, and Their Elements and Phases", by M. Kaga, N.S. Seale, T. Hanawa, J.L. Ferracane, D.E. Waite and T. Okabe, *Dental Materials*, Jan. 1991, pp. 68–72.

"New Surface–Treatment Technologies for Catheters Used for Extracorporeal Detoxification Methods", by R. Bambauer, P. Mestres, R. Schiel and P. Sioshansi, *Dialysis & Transporation*, vol. 24, No. 5, May 1995, pp. 228–237.

"A Large Randomized Clinical Trial of a Silver–Impregnanted Urinary Catheter: Lack of Efficacy and Staphylococcal Superinfection", by D. Riley, D. Classen, L. Stevens and J. Burke, *The American Journal of Medicine*, vol. 98, Apr. 1995, pp. 349–356.

"Frequency, Therapy, and Prevention of Infections Associated with Large Bore Catheters", by R. Bambauer, P. Mestres and K. Pirrung, *ASAIO Journal*, vol. 38, No. 2, Apr.–Jun. 1992, pp. 96–101.

"A New Vascular Access Catheter for Hemodialysis", by R. Uldall, M. DeBruyne, M. Besley, J. McMillan, M. Simons and R. Francoeur, *American Journal of Kidney Diseases*, vol. 21, No. 1993, pp. 001–009.

"Reduced Bacterial Colonization of External Fixation Pins", by E. Tobin, P. Sioshansi, R. Bricault, M. Cannas and A. Masse, *Surfaces in Biomaterials Foundation*, 1995, pp. 19–22.

"Rifampicin Antibiotic Impregnation of the St. Jude Medical Mechanical Valve Sewing Ring: A Weapon Against Endocarditis", by B. French, K. Wilson, M. Wong, S. Smith and M. O'Brien, *The Journal of Thoracic and Cardiovascular Surgery*, vol. 112, No. 2, Aug. 1996, pp. 248–252.

COATED PROSTHETIC CARDIAC DEVICE

This is a Continuation-In-Part of U.S. patent application Ser. No. 08/722,661, filed Sep. 30, 1996 and entitled "COATED PROSTHETIC CARDIAC DEVICE", now abandoned.

FIELD OF THE INVENTION

The present invention relates generally to implantable cardiac prosthetic devices and more particularly to coated devices.

BACKGROUND OF THE INVENTION

The ability to replace or repair diseased heart valves with prosthetic devices has provided surgeons with a method of treating valve deficiencies due to disease and congenital defects. A typical procedure involves the removal of the natural valve and surgical replacement with a mechanical or bioprosthetic valve. Another technique uses an annuloplasty ring to provide structural support to the natural root which supports the natural annulus of the valve.

Studies have shown that structural abnormalities of the heart can render it susceptible to the development of invasive infection of the heart valve called Subacute Bacterial Endocarditis (SBE). The tissue abnormalities can interrupt the blood flow pattern in the heart, generating areas of turbulence and stasis. Transient bacteria can adhere to heart tissues in these areas of abnormal flow and establish an infection (endocarditis). Once endocarditis is established it is extremely difficult to cure. Once the natural valve is damaged by infection, it may need to be replaced. Usually a biological valve is used in these instances for the replacement due to the lower susceptibility of infection.

Following implantation, there is a risk of postoperative systemic infection. Prosthetic Valve Endocarditis (PVE) is an infection that can be associated with a heart valve prosthesis. Heart valves include a fabric sewing cuff or other fabric portion which is used to suture the heart valve to heart tissue. Over time, fibrous tissue grows into the sewing cuff and encapsulates the cuff. Bacteria can colonize in the wound associated with the implant and the fabric of the sewing cuff. Studies have shown that the growth of tissue into the cuff material can attract circulating bacteria or other pathogens. For this reason, heart valve recipients are cautioned regarding activities which may introduce bacteria into their bloodstream, such as dental work.

With respect to replacement heart valves, care must be taken to ensure sterility during production and to prevent contamination during the replacement valve implantation process. For example, to reduce perioperative contamination, some surgeons apply antibiotics prior to implantation. These techniques, however, have relatively short term effectiveness. Others have proposed the use of drug delivery systems designed for antibiotic therapy and these systems are also relatively short-term. In spite of these efforts, PVE occurs in about 2% to 4% of patients.

Other prior art includes U.S. Pat. No. 5,464,438, issued to Menaker. This reference teaches the use of gold metallic coatings on biomedical devices, such as heart valves. This surface treatment is intended to prevent thrombosis.

SUMMARY OF THE INVENTION

In contrast to the use of pharmaceutical products, the present invention includes an antimicrobial metallic coating on portions of the prosthesis, usually fabric, to enhance the overall acceptability of the implantable device. The preferred metal is silver, which is applied to surfaces which are exposed to the heart tissue. Mechanical and bioprosthetic heart valves benefit from this coating and it may also be applied to annuloplasty rings, composite valved grafts, sutures, pledgets, a heart girdle or other implantable devices. The silver-treated portions of these devices inhibit or greatly reduce colonization of endocarditis-causing bacteria without impacting the overall biocompatibility of the device.

BRIEF DESCRIPTION OF THE DRAWINGS

The drawings show exemplary and illustrative prosthetic devices. Throughout the drawings identical reference numerals indicate equivalent structure, wherein.

DETAILED DESCRIPTION OF THE PREFERRED EMBODIMENTS

Figure 1:
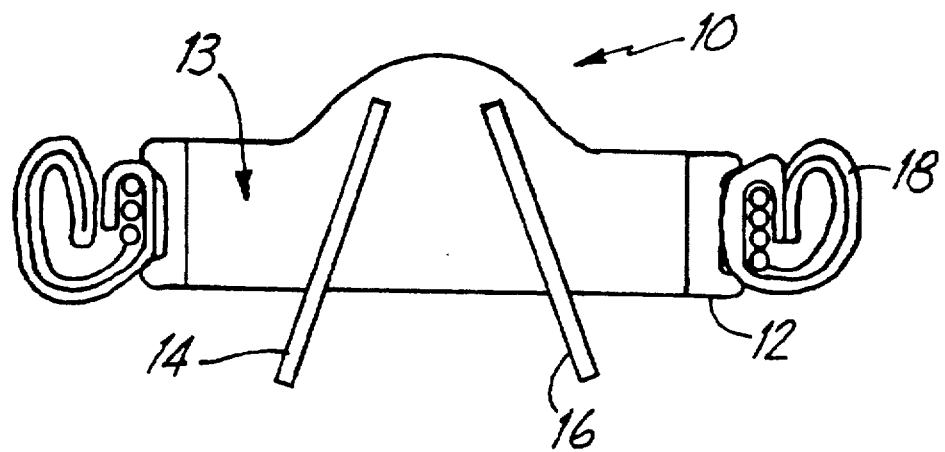
FIG. 1 shows a prosthetic heart valve.

FIG. 1 shows a cross section of a mechanical heart valve 10. The invention is disclosed in the context of a bileaflet valve; however, single and multioccluders are contemplated, as are bioprosthetic heart valves. It should be understood that the techniques presented are applicable to other valve and prosthetic devices. The heart valve 10 includes an orifice ring 12 which forms a blood flow annulus 13. The orifice ring 12 locates and positions a pair of occluders, shown as occluder 14 and occluder 16. The occluders are movable between a first open position and a second closed position. In use, the blood flows through the annulus 13 and controls the position of the two occluders. The sewing cuff 18 of valve 10 will be surgically attached to the heart tissue and ultimately the sewing cuff 18 will become encapsulated by fibrotic tissue.

The suture/sewing cuff or fabric used for any of the prosthetic devices described herein preferably comprises a woven or knitted polyester or polytetrafluoroethylene (PTFE) material, most preferably a woven double velour polyester material, such as obtained from Meadox Medicals, Inc.

There are several ways to provide the silver coating to the devices. First, the fabric used in the construction of the devices may be coated after the fabric is formed. Second, the yarn or fiber that makes up the fabric can be coated before the fabric is formed. Third, after the fabric portion is constructed, the fabric portion itself may be coated with the silver. In addition, the silver coating may be applied directly to a device. In one embodiment, the amount of silver required is quite small, generally in the range of 1–100 mg of silver per gram of fabric, preferably 20–50 mg of silver per gram of fabric. Coating the fiber may be advantageous because this technique may produce a more optimal distribution of the silver in the completed product. For all of the coating methods, the porosity of the textile must be preserved so that tissue ingrowth properties are adequate.

For stented bioprosthetic heart valves, the fabric used for the sewing cuff could be coated in the same manner as described above. It is also contemplated that the stent for these valves may be coated with silver to further enhance the infection resistance of the device. In stentless bioprosthetic heart valves, the outer fabric wraps may also be treated with the silver coating.

Figure 2:
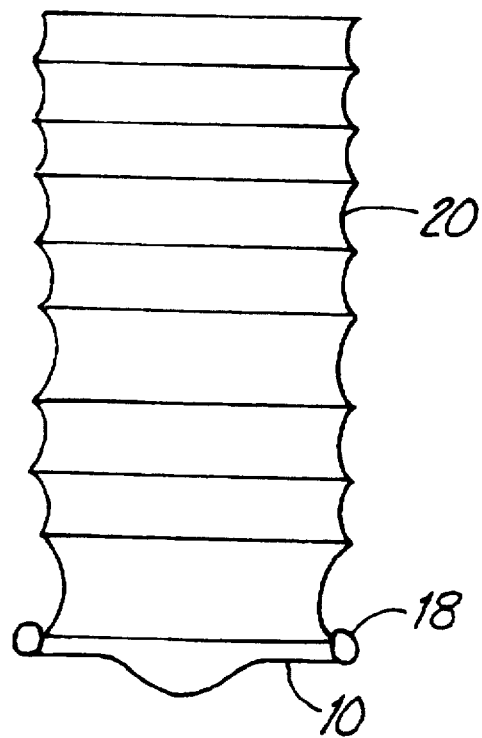
FIG. 2 shows a heart valve with an attached aortic graft.

FIG. 2 shows an aortic valved graft, which includes a mechanical heart valve 10 coupled to a graft 20. The graft 20 portion is preferably made from a polymer, such as woven double-velour polyester material obtained from Meadox Medicals, Inc.. Although the polyester material is well tolerated in some instances, polytetrafluoroethylene (PTFE) material may also be used, depending on surgeon preference. The graft 20 is used for prosthetic replacement or repair of the ascending aorta and must accept other connections, such as coronary anastomosis. After implantation, the graft will be exposed to relatively high-pressure blood flows from the left side of the heart. In general, grafts are coated with different pre-clotting agents, such as collagen or gelatin. In this application, the silver coating may underlie the pre-clotting agent, and its effects, if any, on the resorption rate of the preclotting agent are unknown. It is not clear whether the sealed surface of the graft may impact the benefits of the silver coating, and it is contemplated that silver treatment of only the cuff may be desired in some applications. The silver coating may also be applied directly to collagen or other pre-clotting agents by methods disclosed in co-pending application U.S. Ser. No. 08/794,398, filed Jan. 22, 1997, entitled "Medical Article With Adhered Antimicrobial Metal Ions and Related Methods".

Figure 3:
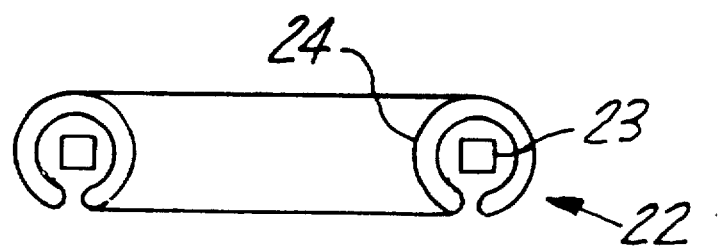
FIG. 3 shows a prosthetic annuloplasty ring.

FIG. 3 is a cross-section of an annuloplasty ring 22 which is generally round. The ring 22 includes an outer layer of fabric 24, such as a woven or knitted polyester, which may surround a frame 23. Unlike the valve prosthesis, the fabric covers the entire external surface of the annuloplasty ring 22. Frame 23 may be rigid, semi-rigid or flexible, and may be made of a metal or a polymer. Examples of polymer frames 23 include high density polyethylene (HDPE), polyethylene terephthalate, or silicone. Metal frames 23 may include, for instance, Elgiloy®, a cobalt, chrome and nickel alloy, or titanium. In use, the annuloplasty ring is used to reconstruct and support the naturally occurring valve annulus, and the entire ring is typically encapsulated by fibrous tissue as a result of the healing response.

Figure 4:
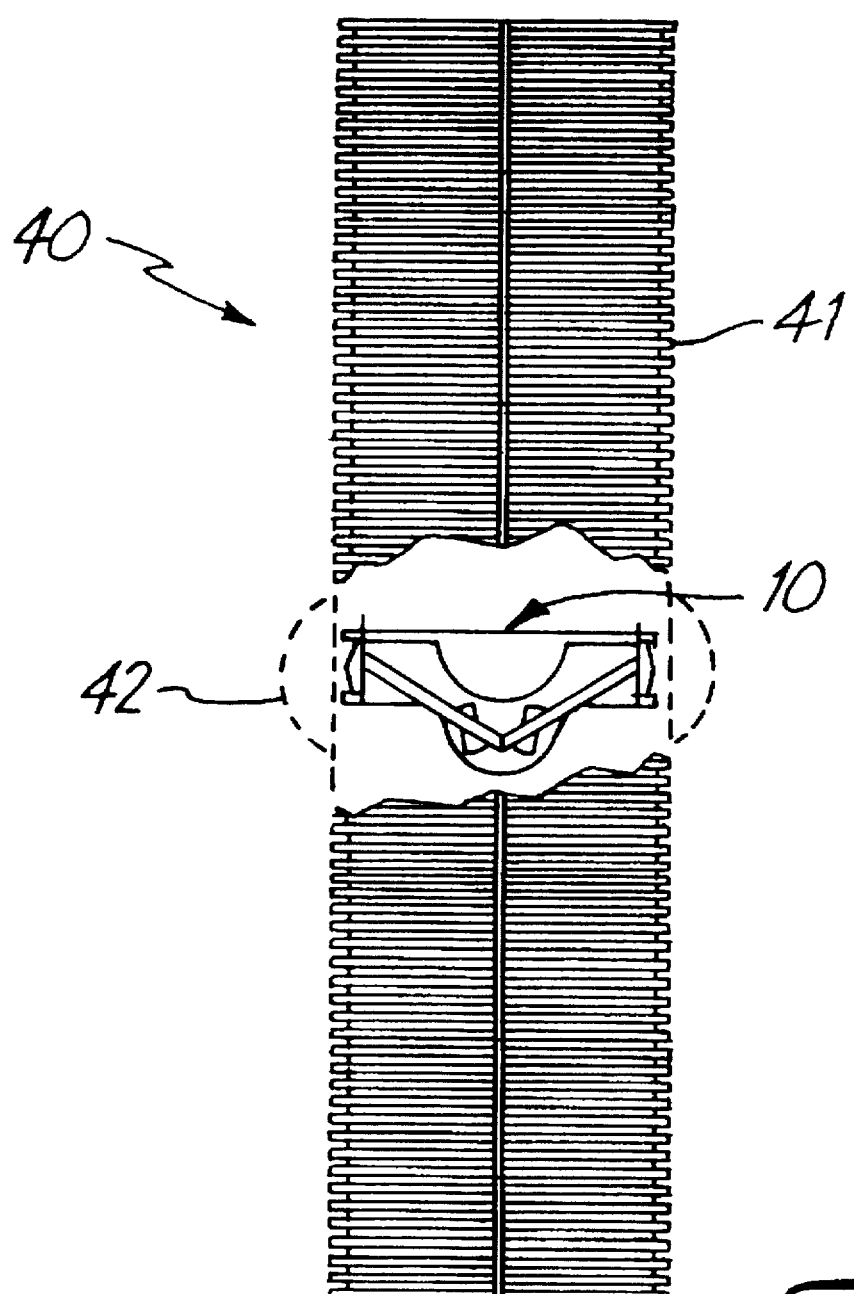
FIG. 4 shows a pulmonic valved graft prosthesis.

FIG. 4 shows a pulmonic valved graft prosthesis 40 in a cutaway view. This type of device 40 is used to repair and reconstruct the pulmonary valve and artery. The valve 10 portion is located in the graft section 41, and a small fabric cuff 42 is located proximate the valve 10 location to assist in implantation of the graft. If a pre-clotting agent is not used, it is preferred that the graft and the cuff 42 be coated with silver.

Figure 5A:
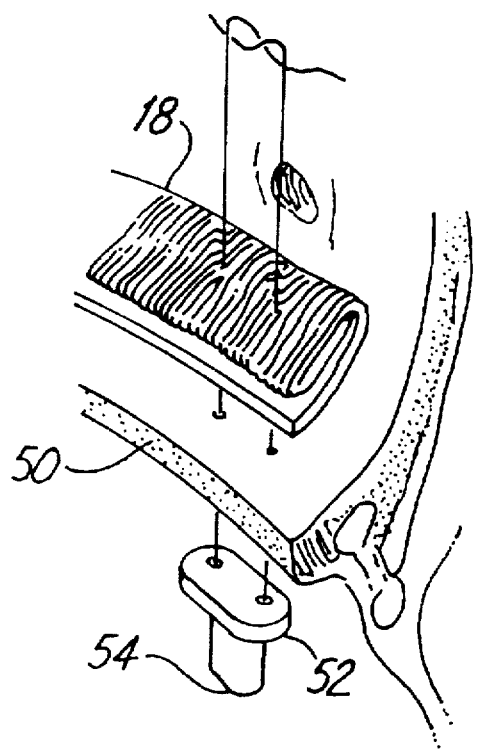
FIGS. 5A and 5B are perspective views showing suturing attachment techniques using a pledget in accordance with the invention.
Figure 5B:
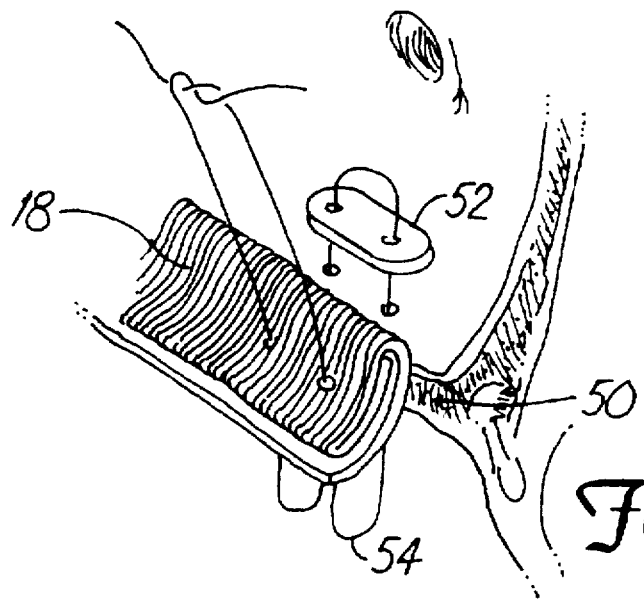

FIGS. 5A and 5B are perspective views showing cuff 18 being sutured to natural heart tissue 50 using pledget 52 and suture 54. FIG. 5A shows an example of a non-everting mattress suturing technique using pledget 52 and suture 54 and FIG. 5B shows an everting mattress suturing technique with pledget 52 and suture 54. One aspect of the invention includes a silver coating of pledget 52 and/or suture 54. In this embodiment, both cuff 18, pledget 52 and suture 54 are coated in accordance with the invention whereby surfaces of natural tissue 50 are only exposed to silver coated surfaces. Typically, pledget 52 is made of polytetrafluoroethylene (PTFE) felt or polyester. Pledgets are widely available in the medical industry, for example, from Ethicon, C. R. Bard and Johnson & Johnson. The present invention is applicable to any type of attachment technique including sutures without pledgets, hooks, staples, clips, clamps or other barbs.

Figure 6:
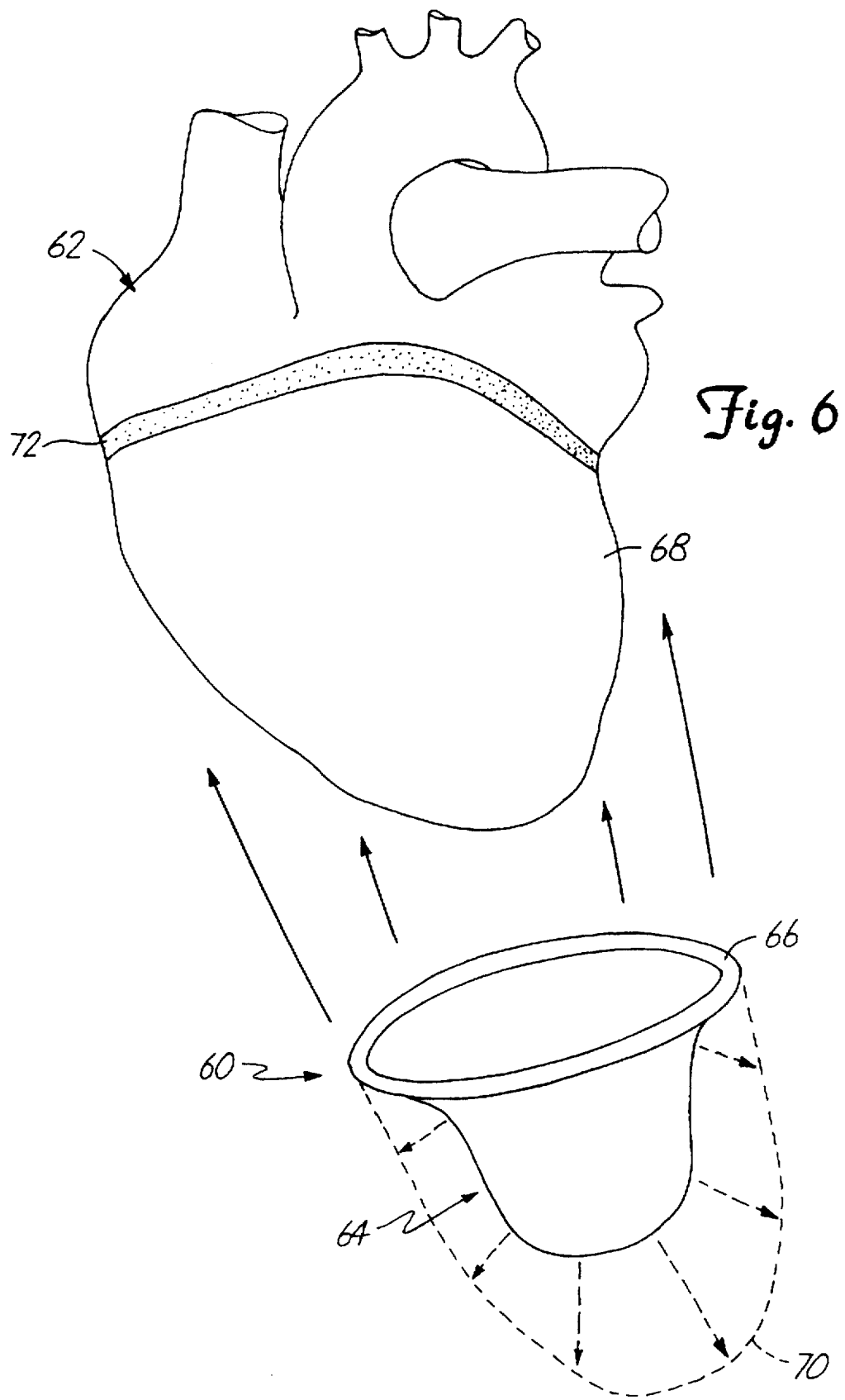
FIG. 6 is an exploded view showing a passive assist device relative to a heart in accordance with one aspect of the invention.

FIG. 6 is a side exploded view of another aspect of the present invention which includes a passive assist device 60 shown with a heart 62. Passive assist device 60 includes girdle 64 and sewing cuff 66 adapted to fit over the ventricular apex 68 of heart 62. Girdle 64 is made of an expandable elastic, biocompatible material such as a polymer, rubber, pericardial tissue, stretchable polyester fabric, etc. and expands to expanded profile 70 when placed over ventricular apex 68. Sewing cuff 66 may be of any suitable cuff material such as described above including an annuloplasty ring adapted for suturing to fibrous plane 72. Passive assist device 60 is designed to provide increased myocardial contractility of a failing heart. Girdle 64 surrounds the ventricles with a highly elastic, biocompatible material to provide a squeezing force during systole. In some embodiments, device 60 is coated to make it more biocompatible and less thrombogenic. Those skilled in the art will recognize that any type of direct myocardial attachment, such as to the fibrous plane, may be used to attach the girdle to the heart including suture, staples, glue, etc. Device 60 may be coated with materials including silver or other antimicrobial metals, peptides, and sulfonated hydrogels.

It has been discovered that coating portions of cardiovascular prostheses with a thin adherent film of silver provides protection from infection of the device. In some instances, the entire fabric member of the prosthetic device may not be coated with the silver, such as in areas of suture markings. In addition, in vivo experiments have shown excellent tissue ingrowth, without excessive thrombus formation. Minimal migration of silver into surrounding tissue may provide further anti-microbial protection.

The thin film silver coating may be deposited or carried in the fabric member, fibers, or sewing cuff using methods known to the art. Throughout this application the term "coating" or "coated" may be used to mean that the silver may be coated on the surface of the device or component or may be implanted within or into the device or component as well as on the surface of the device or component, depending on how the silver was applied. For instance, the silver coatings may be applied by vapor-deposition or by sputtering. The use of the vapor-deposition technique is described in U.S. Pat. No. 4,167,045 to Sawyer. Although any of a number of techniques can be used to create the silver coating, it is important that the coating be extremely adherent to the fabric or other materials to prevent excessive circulation of the cytotoxic silver material throughout the body, while retaining porosity necessary for tissue ingrowth.

Vapor deposition of metal using ion acceleration transfer systems (under high-vacuum) are well known at this time. U.S. Pat. No. 5,474,797 assigned to Spire Inc. may be referred to for techniques suitable for the application of silver to fabric material.

Figure 7:
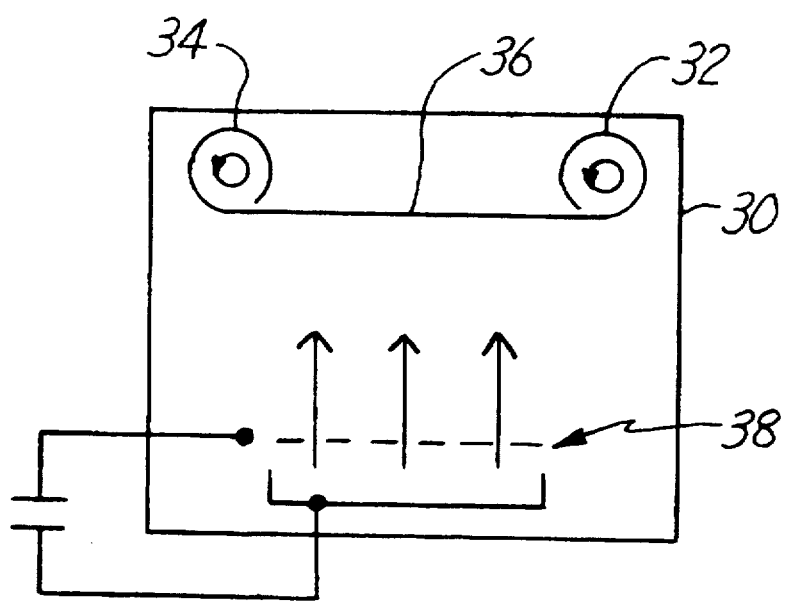
FIG. 7 shows an apparatus for coating fiber or fabric.

FIG. 7 shows an illustrative but not limiting example of one technique for coating fiber. The treatment chamber 30 includes a supply reel 32 and a take up reel 34. The fiber 36 is moved from one reel to the other while silver atoms are accelerated by ion source 38 and directed electrically to the fiber 36. As is known in this art, other metals may be adhered to the fiber before the coating of silver is applied. Similar methods may be employed for coating the fabric or the assembled sewing cuff by utilizing fixtures, such as a mandrel, to rotate or position the fabric or cuff to provide a uniform coating of silver.

To achieve a uniform and tightly adherent silver coating, vapor deposition techniques, such as ion beam implantation and ion beam-assisted deposition (IBAD) are contemplated within this disclosure and ion beam-assisted deposition is most preferred.

It is understood that traditional coating techniques, such as sputtering, may result in areas of the fabric or device which are not well coated or areas where an excess of silver is deposited. While the uniform distribution, of silver atoms throughout the treated portion of the prosthesis is believed to be beneficial for this prosthetic application, a distribution which is not uniform may also be acceptable. Coating the fiber or yarn used to make the treated portion of the prosthesis addresses this problem and may result in a more uniform distribution of silver in the treated portion. It is possible to form the fabric used to manufacture the sewing cuff 18 or other portion of the cardiovascular prosthetic devices described above in a conventional fashion.

The alternative procedure of coating the fabric or sewing cuff after it is woven is contemplated as an alternative technique within the scope of this disclosure. In this embodiment, porosity necessary for adequate tissue ingrowth must be maintained.

In one embodiment, the silver will slightly oxidize, providing an enhanced biologically active antiseptic surface. For example, a representative silver coated Dacron® polyester sample showed silver oxide present at 9% and metallic silver species present at 91%. Although the electrical properties of this surface are not well characterized, it is expected that the electrical conductivity may serve important biological functions as well. When combined with other materials, the silver may ionize more readily, increasing the antimicrobial effectiveness.

EXAMPLE 1

A double velour woven polyethylene terephthalate (Meadox Part Number 33 FR) (polyester) fabric was obtained from Meadox Medicals, Inc. Silver was applied using an ion beam-assisted deposition process as described in U.S. Pat. No. 5,474,797.

Two different assays were performed to determine the anti-microbial effectivity of the silver-coated fabric. In the Dow Corning Corporate Test Method 0923, three 750 mg samples of silver-coated fabric (Sample No. 1 in Table 1) and three 750 mg samples of uncoated fabric (Sample No. 2 in Table 1) were individually exposed to a 75 ml solution containing either: *Staphylococcus epidermis* ATCC 29886, *Streptococcus pyogenes* ATCC 8668, or *Candida albicans* ATCC 10231 at a concentration of $(1-2)\times10^4$ CFU/ml.

TABLE 1

| Test Organism | Sample Number | Bacterial Count (CFU/mL) Zero Time | One Hour | Percent Reduction |
|---|---|---|---|---|
| *Staphylococcus epidermis* ATCC 29886 | #1 | 23,000 | 1,200 | 94.78 |
| *Staphylococcus epidermis* ATCC 29886 | #2 | 20,000 | 15,000 | 25.00 |
| *Streptococcus pyogenes* ATCC 8668 | #1 | 16,000 | 90 | 99.44 |
| *Streptococcus pyogenes* ATCC 8668 | #2 | 16,000 | 16,000 | NR |
| *Candida albicans* ATCC 10231 | #1 | 14,000 | 360 | 97.43 |
| *Candida albicans* ATCC 10231 | #2 | 11,000 | 12,000 | NR |

As shown in Table 1, the bacterial count was determined at time zero and one hour after inoculation to determine the percent reduction in bacteria. The results indicate a 95% to 99% reduction in bacteria on the silver-coated fabric as compared to the control (uncoated) samples which only showed up to a 25 percent reduction of bacteria.

In the NYS63 Test for Bacteriostatic Activity, one-inch square pieces of silver-coated fabric were exposed to each of the following organisms at the indicated concentrations:

*Staphylococcus epidermis* ($5.8\times10^4$ CFU/0.2 ml),

*Streptococcus pyogenes* ($2.8\times10^4$ CFU/0.2 ml), or

*Candida albicans* ($3.0\times10^4$ CFU/0.2 ml).

TABLE 2

| Replicate # | 24-Hour Organism Count | | Percent Reduction | |
|---|---|---|---|---|
| | *S. epidermidis* | *S. pyogenes* | *S. epidermidis* | *S. pyogenes* |
| 1 | $7.0 \times 10^2$ | $<1.0 \times 10^2$ | 98.79 | 99.64 |
| 2 | $<1.0 \times 10^2$ | $<1.0 \times 10^2$ | 99.83 | 99.64 |
| 3 | $2.0 \times 10^2$ | $<1.0 \times 10^2$ | 99.66 | 99.64 |
| 4 | $1.0 \times 10^2$ | $<1.0 \times 10^2$ | 99.83 | 99.64 |
| 5 | $2.5 \times 10^2$ | $<1.0 \times 10^2$ | 99.57 | 99.64 |

| Replicate # | 24-Hour Organism Count *C. albicans* | Percent Reduction *C. albicans* |
|---|---|---|
| 1 | $<1.0 \times 10^2$ | 99.67 |
| 2 | $<1.0 \times 10^2$ | 99.67 |
| 3 | $<1.0 \times 10^2$ | 99.67 |
| 4 | $5.0 \times 10^2$ | 98.33 |
| 5 | $1.9 \times 10^3$ | 93.67 |

As shown in Table 2, the total remaining bacterial count was determined twenty-four hours after exposure. The results indicate a 94% to 99.8% reduction in the organism for the silver-coated fabric.

EXAMPLE 2

Fabric was coated, as described in Example 1, and was used to fabricate a sewing cuff which consisted of half silver-coated and half uncoated polyester fabric. The hybrid cuff was assembled to a St. Jude Medical® mechanical heart valve prosthesis.

Blood compatibility and tissue ingrowth characteristics were assessed after 30 days in a sheep mitral valve model. Tissue reaction to the control and treated (coated) portions were assessed grossly and histopathologically. Sewing cuff specimens were embedded in plastic, sectioned and stained with hematoxylin and eosin for histopathological analysis. Results indicated that healing was similar to the coated fabric as compared to the uncoated fabric with respect to tissue ingrowth and blood compatibility, indicating that the silver does not affect the safety of the device.

A hybrid valve similar to the polyester valve described above was made utilizing a PTFE cuff. Again, half the cuff was coated with silver and half was uncoated. The valve was implanted in the mitral sheep model for 30 days. Gross examination showed healing and tissue response similar to those for the polyester cuffs and valve.

The present invention has several advantages. Placement of a thin film, tightly adherent silver coating onto the various biomedical prostheses provides anti-microbial properties to the device. As a result, a mechanical heart valve may be used in situations where other devices have been preferred, such as in cases of active endocarditis, thus providing more options for the surgeon and the patient. For example, homografts have been the preferred device for replacement of a valve in a patient with active endocarditis. Homografts are in low supply, high demand and are typically reserved for pediatric cases. Thus, having a prosthetic device with an antimicrobial coating provides a significant new option for adult endocarditis cases. The low leaching of the silver from the prosthetic device provides sustained effects, which further enhances the anti-microbial properties of the device. The silver coating does not affect the substrate to which it is attached. Further, use of a silver coating on prostheses has shown a significant reduction in bacteria. This invention will also reduce surgical time in cases where surgeons dip the valves into an antibiotic solution, since it will eliminate this step.

Although the present invention has been described with reference to preferred embodiments, workers skilled in the art will recognize that changes may be made in form and detail without departing from the spirit and scope of the invention. For example, even though vapor deposition has been described as the preferred method for applying the silver, other methods including chemical methods are within the contemplation of this invention, including dipping the fibers or fabric into a solution in which silver is dissolved, or impregnating or immersing the fiber or fabric in a silver solution, electroplating, or incorporating silver particles within the fabric/cuff. Further, the invention may be implemented with antimicrobial materials other than silver such as Au, Pt, Pd, Ir (i.e., the noble metals), Cu, Sn, Sb, Bi and Zn or alloys thereof. Further, the inventive silver coating or silver implantation may be used in any device for implantation in or proximate to a natural heart and is not limited to the specific devices set forth herein. The inventive passive assist device is particularly useful because the device is not homographic and will provide additional options, particularly for adult patients.

What is claimed is:

1. An implantable heart prosthesis, said prosthesis comprising:
    an orifice ring having an outer periphery and an inner periphery, said ring defining an annulus;
    said annulus defining a passage for the flow of blood;
    a fabric member coupled to at least said outer periphery of said orifice ring and adapted for coupling to a patient's heart tissue for an extended duration;
    said fabric member carrying silver to thereby substantially inhibit microbial growth on the fabric member.

2. The prosthesis of claim 1 wherein said fabric is coated with silver in an ion beam-assisted, high-vacuum environment, such that said silver atoms are inserted into the surface of said fabric.

3. The device of claim 1 wherein said fabric is coated with silver in a high-vacuum environment, such that said silver atoms are coated on the surface of said fabric.

4. The prosthesis of claim 1 wherein said fabric member comprises a plurality of fibers carrying silver.

5. The prosthesis of claim 4 wherein said fabric is woven from polyester fibers.

6. The prosthesis of claim 1 further including:
    a first occluder;
    a second occluder;
    said first and second occluders mounted for motion within said ring;
    a sewing cuff coupled to said ring; and
    said sewing cuff carrying silver thereon.

7. The prosthesis of claim 1 wherein the device comprises a heart valve.

8. The device of claim 7 further including:
    a graft coupled to said ring; and
    said graft fabricated from said silver coated fabric.

9. The prosthesis of claim 1 further comprising a stent.

10. The device of claim 1 wherein the device comprises an annuloplasty ring.

11. The prosthesis of claim 1 wherein the device comprises a bioprosthetic valve.

12. The device of claim 1 wherein the device comprises a valved graft.

13. The prosthesis of claim 1 wherein the fabric member comprises a sewing cuff.

14. The prosthesis of claim 1 including a pledget carrying silver adapted to cooperate with the fabric carrying member for attaching the implantable heart prosthesis to natural tissue of a patient.

* * * * *